United States Patent [19]
Ostiguy, Jr. et al.

[11] Patent Number: 6,162,256
[45] Date of Patent: Dec. 19, 2000

[54] ACETABULAR PROSTHESIS

[75] Inventors: Pierre S. Ostiguy, Jr., Rochester; Robert E. Sommerich, Norton, both of Mass.

[73] Assignee: Depuy Orthopaedics, Inc., Warsaw, Ind.

[21] Appl. No.: 08/998,879

[22] Filed: Dec. 29, 1997

[51] Int. Cl.$^7$ ........................................ A61F 2/32
[52] U.S. Cl. ........................ 623/22.26; 623/22.28
[58] Field of Search ............................ 623/22, 23, 18, 623/19, 22.21, 22.44, 22.26, 22.28

[56] References Cited

U.S. PATENT DOCUMENTS

| | | | |
|---|---|---|---|
| 4,770,661 | 9/1988 | Oh | 623/23 |
| 4,840,630 | 6/1989 | Kitamura | 623/22 |
| 4,936,855 | 6/1990 | Sherman | 623/18 |
| 5,080,677 | 1/1992 | Shelley | 623/22 |
| 5,108,447 | 4/1992 | Zeiler et al. | 623/23 |
| 5,507,826 | 4/1996 | Besselink et al. | 623/18 |
| 5,658,338 | 8/1997 | Tyllos et al. | 623/18 |
| 5,766,260 | 6/1998 | Whiteside . | |

FOREIGN PATENT DOCUMENTS

| | | |
|---|---|---|
| 0139356 | 5/1985 | European Pat. Off. . |
| 0436317 | 7/1991 | European Pat. Off. . |
| 0680735 | 11/1995 | European Pat. Off. . |
| 0728448 | 8/1996 | European Pat. Off. . |

*Primary Examiner*—John J. Wilson
*Assistant Examiner*—Eduardo C. Robert
*Attorney, Agent, or Firm*—Nutter, McClennen, & Fish, LLP

[57] ABSTRACT

An acetabular prosthesis has a shell component that is implantable within bone and a liner component that is matable to the shell. The shell has a generally convex bone engaging outer surface and a generally concave inner surface. A groove is formed in the inner surface of the shell and extends about at least a portion of the inner circumference of the shell. The liner has an inner concave surface and an outer, convex surface with a shape complementary to and matable within the inner surface of the shell. One or more deformable positive surface features is formed on the outer surface of the liner, adapted for selective mating with the slot of the shell. The liner may be joined to the shell by press fitting the two components together such that the positive surface features engage the groove.

13 Claims, 5 Drawing Sheets

ACETABULAR PROSTHESIS

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to joint prostheses and more particularly to acetabular prostheses useful for partial or total replacement of the hip joint.

BACKGROUND OF THE INVENTION

Acetabular prostheses are known for use as a component for a total hip prosthesis. Acetabular prostheses typically include two separate components, one of which is a cup or shell that is affixed within a cavity reamed in healthy bone of the acetabulum. The acetabular cup may have an external (i.e., bone-contacting) geometry that is appropriate for a given patient. The inner geometry of the acetabular cup is usually characterized by a smooth, generally spherical cavity. The acetabular cup is typically made of a metal or metal alloy. In some cases, however, polymeric acetabular cups are utilized.

A liner component is often mated with the inner geometry of the acetabular cup to provide a low friction bearing surface that articulates with a femoral head. The liner may have an outer, spherical surface that is of a size and shape to enable it to mate with the inner surface of the acetabular cup. The inner surface of the liner likewise is hemispherically shaped, having a smooth, low friction surface. As noted above, the femoral head seats within and articulates with the internal surface of the liner.

Acetabular cups are often made from a metal or metal alloy. Some designs, however, utilize polymeric cups. One polymer commonly used to form the liner is ultrahigh molecular weight polyethylene. However, it is also possible to fabricate the liner from other materials, including metals, metal alloys and ceramics.

Regardless of the materials and geometries used for the acetabular prosthesis, the acetabular cup and liner must be joined together, usually during the course of a surgical procedure. That is, a surgeon first implants the acetabular cup within the patient's acetabulum. Thereafter, the liner is separately affixed within the acetabular cup. A variety of liner designs exist and many are not symmetrical. Thus, the surgeon must determine the appropriate orientation of the liner with respect to the cup. Once the liner is properly oriented, it must remain so after affixation to the cup.

Some acetabular prosthesis designs do not permit easy mating of the liner to the cup; the mating of some designs can, in fact, be quite challenging. Specialized tools or separate components may be necessary to join these components or to permanently affix them together. These additional steps may render the attachment process more time-consuming and may introduce the possibility that the liner and the shell will become misaligned due to surgical technique or for other reasons. Further, there is always a possibility that the joinder mechanism may fail to achieve its objective to secure the two components to one another.

A number of patents describe acetabular prostheses designs that utilize a separate component to lock the liner and the shell together. Examples of such patents include U.S. Pat. Nos. 4,619,658; 4,770,658; 4,784,663; 4,969,910; 5,049,158; 5,171,285; 5,263,988; 5,425,779; 5,507,826; and 5,658,348.

Other known designs do not require a separate locking mechanism to join the liner and the cup. Instead, an interference fit or another form of mechanical engagement of the two components is relied upon. Examples of patents disclosing such attachment mechanisms include U.S. Pat. Nos. 4,172,296; 4,650,491; 5,376,122; 5,443,519; and 5,549,698.

Despite the acetabular prostheses designs that are known to exist, there is still a need for an acetabular prosthesis design that provides excellent attachment strength between the liner and the cup while at the same time providing ease of assembly without the need for additional assembly tools or components.

SUMMARY OF THE INVENTION

An acetabular prosthesis has a shell component that is implantable within bone and a liner component that is matable to the shell. The shell has a generally convex bone engaging outer surface and a generally concave inner surface. At least one groove is formed in the inner surface of the shell and extends about at least a portion of the inner circumference of the shell. The liner, which has a polar region and an equator region, has an inner concave surface and an outer, convex surface with a shape complementary to and matable within the inner surface of the shell. At least one deformable positive surface feature is formed on the outer surface of the liner, adapted for selective mating with the slot of the shell. Each deformable positive surface features has a superior end and an inferior end, both of which protrude from the other surface of the line component. The inferior end preferably is cantilevered such that an inner surface of the inferior end is separated from the outer surface of the liner component by a gap. The liner may be joined to the shell by press fitting the two components together such that the positive surface features engage the slot.

The prosthesis may also have a structure to prevent rotation of the liner with respect to the shell after joinder of the two components. The anti-rotation mechanism may be in the form of one or more tabs in the outer surface of the liner, adjacent to the positive surface features. At least one recess is formed in the shell with a size and shape complementary to the tabs such that each tab is matable within one of the recesses.

One advantage of the prosthesis of the present invention lies in its ease of assembly and its ability to provide good attachment strength between the liner and the shell.

DETAILED DESCRIPTION OF THE INVENTION

Figure 1A:
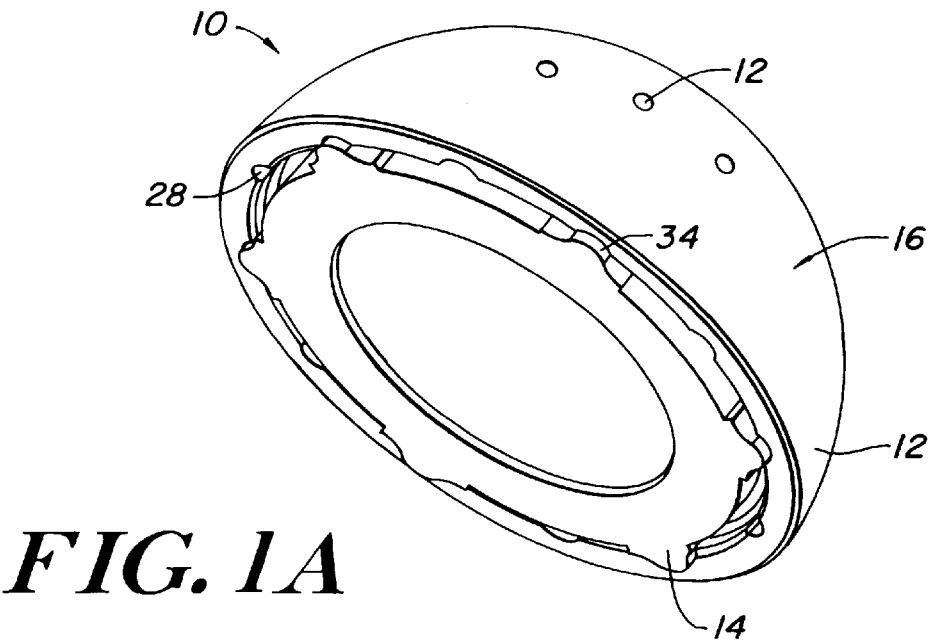
FIG. 1A is a perspective view of an acetabular prosthesis according to the present invention in which an acetabular shell component is joined to a liner component.
Figure 1B:
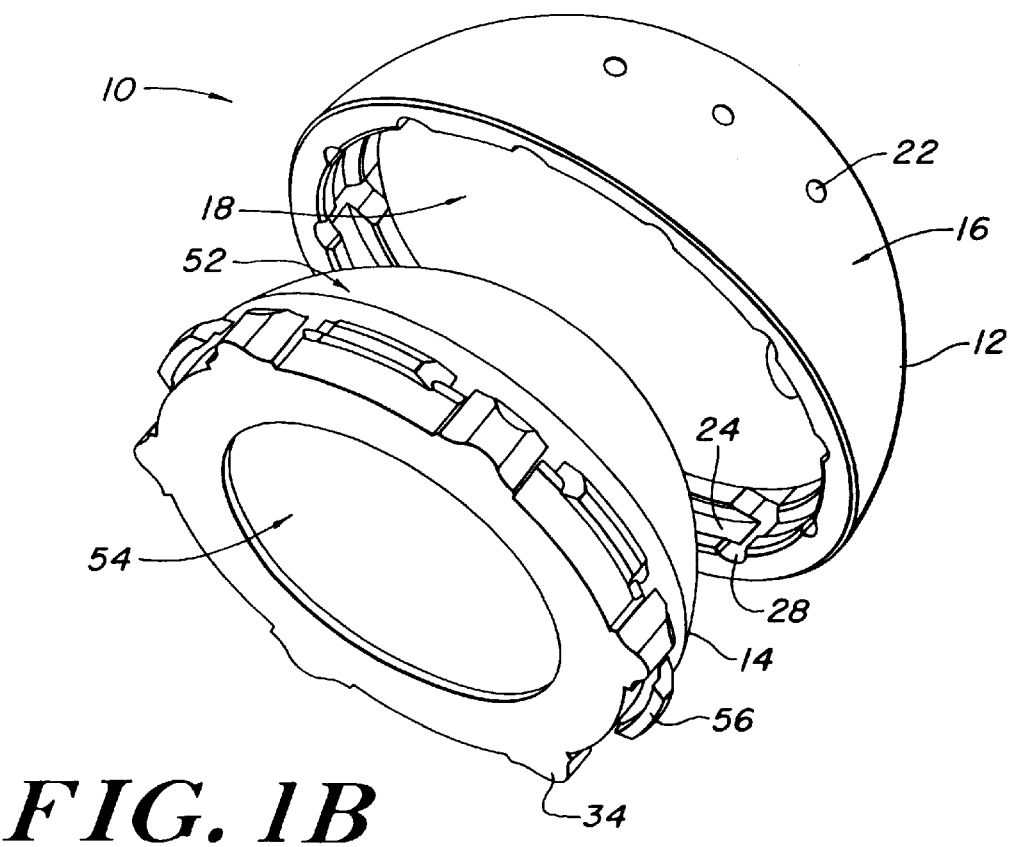
FIG. 1B is a perspective view of the acetabular prosthesis of FIG. 1A in which the acetabular shell component is separated from the liner component.
Figure 2:
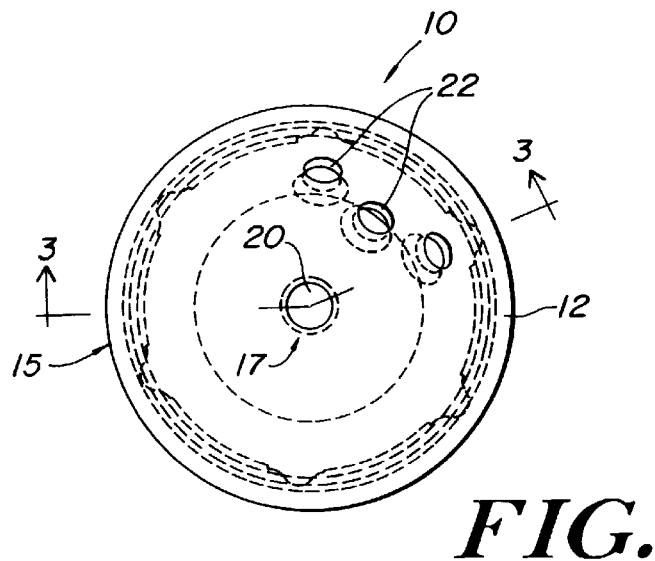
FIG. 2 is a top view of the acetabular prosthesis shown in FIG. 1A.
Figure 3:
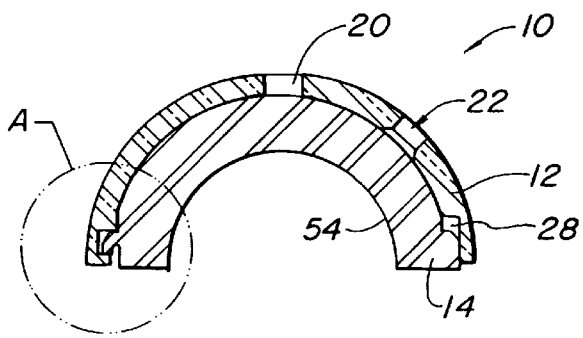
FIG. 3 is an elevated sectional view of the prosthesis shown in FIG. 2, at lines 3—3.
Figure 4:
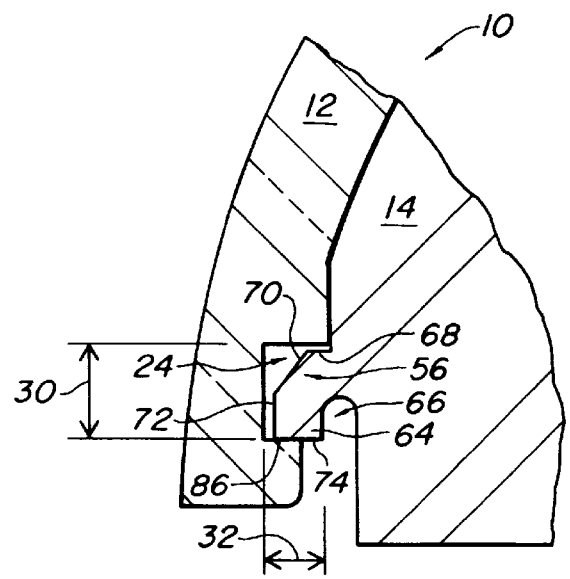
FIG. 4 is a detailed view of portion A of the prosthesis shown in FIG. 3.

The present invention provides an acetabular prosthesis with an effective and convenient mechanism for joining and securing the acetabular shell and liner components to each other. Referring to FIGS. 1A through 4, the acetabular prosthesis 10 includes an acetabular shell 12 and a liner 14 which are selectively attachable to one another through an interlocking engagement.

The acetabular shell 12, illustrated in FIGS. 5 through 8A, is a substantially hemispherical member having a generally convex outer bone-engaging surface 16. Opposite the outer surface 16 is a generally hemispherical, substantially concave inner surface 18. The shell may be characterized as having an equator region 15 and a polar region 17. Further, the shell includes an equatorial axis 19 and a polar axis 21.

Figure 5:
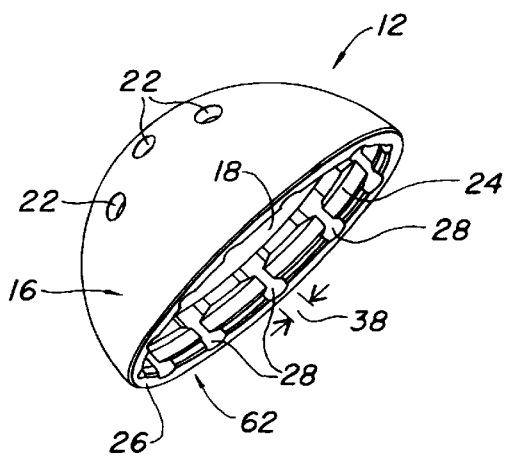
FIG. 5 is a perspective view of a shell component useful with the acetabular prosthesis of the invention.
Figure 6:
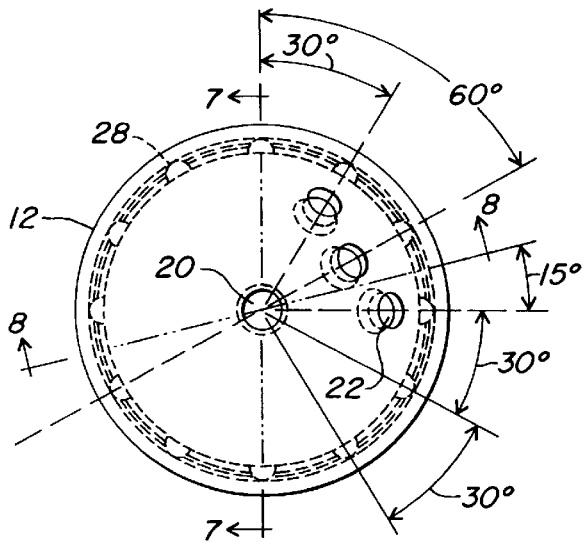
FIG. 6 is a top view of the shell component of FIG. 5.
Figure 7:
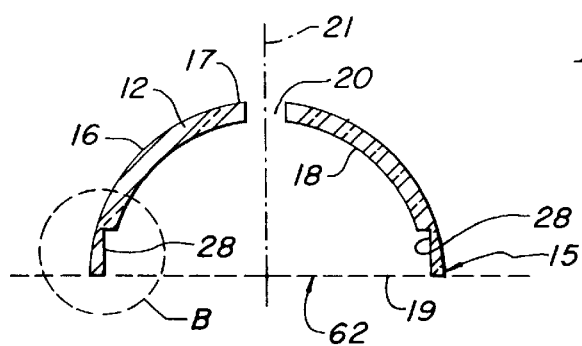
FIG. 7 is an elevated sectional view of the shell component of FIG. 6 at lines 7—7.
Figure 7A:
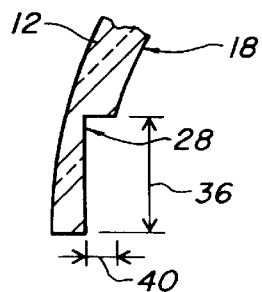
FIG. 7A is a detailed sectional view of portion B of the shell component of FIG. 7.
Figure 8:
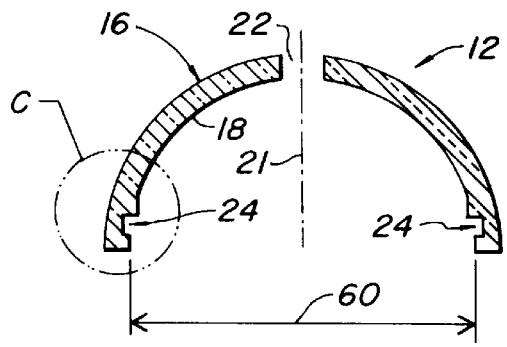
FIG. 8 is an elevated sectional view of the shell component of FIG. 6 at lines 8—8.
Figure 8A:
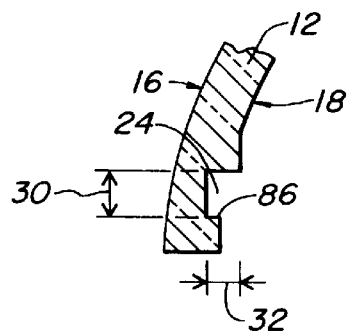
FIG. 8A is a detail or sectional view of portion C of the shell component of FIG. 8.

The outer surface 16, as shown in FIGS. 5 and 6, may include an apical hole 20 for seating an apical screw. One or more additional holes 22, effective to seat bone screws, may also extend through outer surface 16. The outer surface of the shell may further include surface features (not shown), such as ridges, to optimize fixation to bone and/or to encourage bone ingrowth. One of ordinary skill in the art will readily appreciate that a variety of additional surface features, in addition to ridges, can be formed on the outer surface to optimize performance of the prosthesis.

The inner surface 18, as shown in FIGS. 4, 5 and 7–8A, includes a groove 24 that extends substantially parallel to the equatorial axis 19. The groove 24 may be continuous or it may be formed of discrete elements. Further, the groove 24 may extend partially or entirely around the circumference of the shell, either continuously or in discrete sections. In the illustrated embodiment, the groove 24 is disposed in the equatorial region 15, and is spaced from the rim 26 of the shell, in the direction towards the polar region 17. Further, the embodiment of FIG. 5 illustrates that the groove 24 is interrupted by recesses 28, which extend perpendicular to the equatorial axis 19.

In one embodiment, the groove 24 begins a distance of about 0.5 to 10 mm from the rim 26, in the direction towards the polar region 17. The dimensions of the groove will vary depending upon variables such as the dimensions of the shell, the dimensions of the liner and the dimensions of certain surface features present on the liner. In one embodiment, however, the groove 24 has a height 30 in the range of about 2 to 4.5 mm and a depth 32 of about 4 to 8 mm.

The grooves may be separated from each other by about 0° to 180°, with 0° separation representing a continuous groove.

The recesses 28 are intended to seat anti-rotation tabs 34 present on the liner 14, as discussed below, to prevent rotation of the liner 14 relative to the acetabular shell 12. The recesses 28 extend from the rim 26 towards the pole region 17. The height 36 of the recesses may be about 2 to 8 mm while the width 38 is about 2 to 5 mm. The depth 40 of the recesses may be in the range of about 1 to 5 mm.

The shell 12 can be made from a variety of suitable materials. Generally, however, it is made from metals or metal alloys known to those having ordinary skill in the art.

The liner 14, as shown in FIGS. 9 through 12A, has an equatorial region 42 and a rim 44. Opposite the equator region 42 is a polar region 46. An equatorial axis 48 of the liner extends parallel to the equatorial region 42 while a polar axis 50 extends perpendicular to the equatorial axis 48. The liner also has a convex outer surface 52, which is substantially hemispherically shaped and complementary to inner surface 18 of shell 12. Further, the liner 14 has a concave inner surface 54 which is intended to seat a femoral head of a hip prosthesis (not shown). One of ordinary skill in the art will appreciate that the inner surface 54 should be a smooth, low friction surface.

The liner 14, as illustrated in FIGS. 9 through 12A, includes one or more anti-rotation tabs 34 which protrude from the outer surface 14. The tabs 34 can be of virtually any shape that is complementary to and matable within the recesses 28 of the shell 12. Accordingly, the tabs 34 protrude from the outer surface of the liner by about 1 to 5 mm and have a width in the range of about 2 to 5 mm.

Tabs 34 may be positioned at virtually any location on the outer surface 52 of the liner 14. In one embodiment, the tabs 34 are positioned adjacent to the equatorial region 42, spaced approximately 0.5 to 10 mm from the rim 44 in the direction towards the polar region 46.

As noted above, the anti-rotation tabs 34 cooperate with the recesses 28 to prevent rotation of the liner 14 relative to the shell 12. No specific number of anti-rotation tabs 34 and recesses 28 is necessary to prevent rotation of the liner 14 relative to the shell 12 since any number will accomplish this objective. Generally, however, more than one anti-rotation tab 34 is present and from four to nine anti-rotation tabs can be used, depending upon the size of the liner and the shell.

The outer surface 52 of the liner 14 also includes at least one deformable positive surface feature 56. The positive surface feature 56 cooperates with the groove 24 of shell 12 to selectively attach the liner to the shell. In one embodiment, discussed below, only an edge portion of the surface 56 feature is deformable. Further, the positive surface feature 56 protrudes from the outer surface 52 of the liner 14 by a distance sufficient to prevent noninterfering insertion of the liner 14 within the shell 12. That is, the outer diameter 58 of the liner, measured at the surface feature 56, is greater than both the nominal diameter 51 of the liner and the inner diameter 60 of the opening 62 of the shell. The positive surface feature 56 should protrude from the outer surface 52 of the liner by a distance of about 1 to 3 mm. Similarly, the outer diameter 58 of the liner measured at the surface feature 56 should exceed the inner diameter 60 of the opening 62 by about 2 to 4 mm.

The positive surface feature 56 may be a continuous structure, or it may be present on the outer surface of the liner in discrete sections. Further, the positive surface feature 56 may extend partially or completely about the circumference of the liner, either continuously or in discrete sections. When present in discrete sections, the length 57 of each separate positive surface feature 56 is about 3 to 9.5 mm.

The deformable positive surface feature 56 may take on a variety of shapes. In the embodiment illustrated in FIGS. 9 through 12A, a deformable portion 64 is cantilevered such that it is separated by a group 66 from the outer surface 52 of liner 14.

Figure 9:
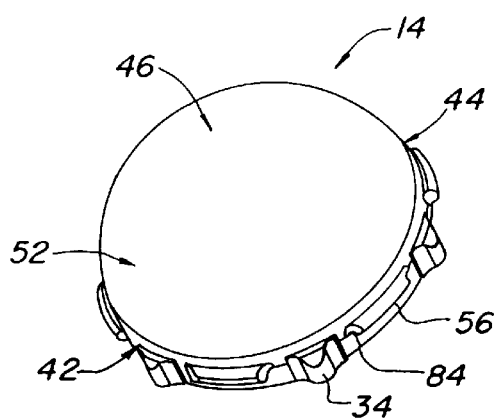
FIG. 9 is a perspective view of a liner component useful with the acetabular prosthesis of the invention.
Figure 10:
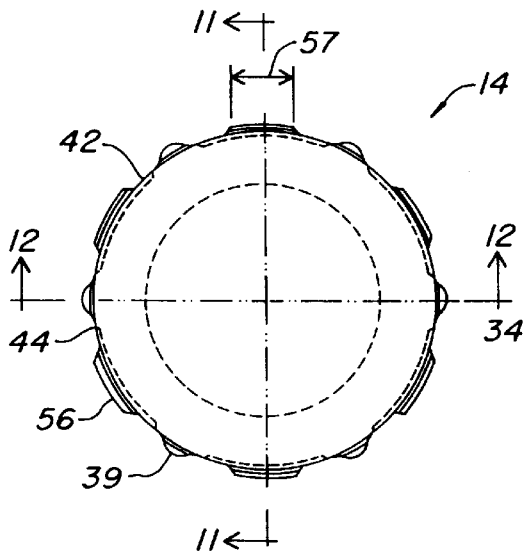
FIG. 10 is a top view of the liner component shown in FIG. 9.
Figure 12:
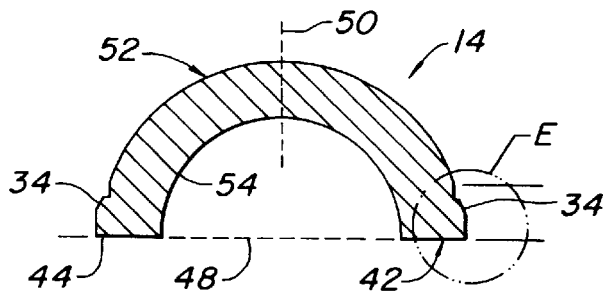
FIG. 12 is an elevated sectional view of the liner component shown in FIG. 10, at line 12—12.
Figure 12A:
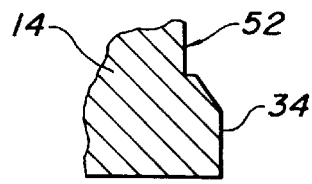
FIG. 12A is a detailed sectional view of portion E of the liner component of FIG. 12.
Figure 11:
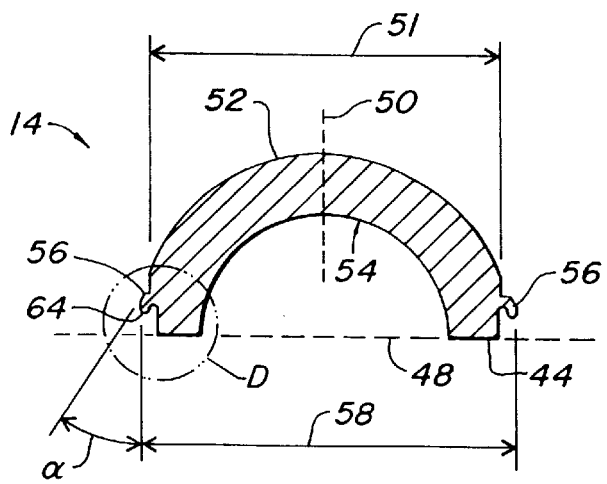
FIG. 11 is an elevated sectional view of the liner component shown in FIG. 10, at lines 11—11.
Figure 11A:
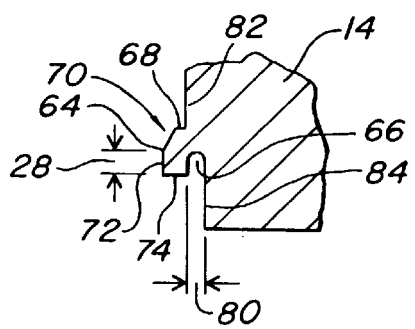
FIG. 11A is a detailed sectional view of portion D of the liner component shown in FIG. 11.

As best shown in FIGS. 9, 10 and 11A, the surface feature 56 has a superior wall 68 which is oriented substantially parallel with equatorial axis 48. Adjacent and inferior to superior wall 68 is a canted intermediate wall 70, which may be oriented at an angle ($\alpha$) in the range of about 30 to 45 degrees to facilitate insertion of the liner 14 within the shell 12. A vertical intermediate wall 72 is adjacent canted intermediate wall 70. The vertical intermediate wall 72 may be substantially parallel to the polar axis 50. The positive surface feature terminates in an inferior wall 74 which, like the superior wall 68, is substantially parallel to equatorial axis 48.

The dimensions of the positive surface feature and its various elements may vary depending upon the sizes of shell 12 and liner 14 as well as the desired attachment strength. As, noted above, a number of discrete positive surface features 56 may extend about the circumference of the outer surface 52 of the liner 12. FIG. 9 illustrates an embodiment where each surface feature 56 extends about the circumference of the outer surface 52 for approximately 30 degrees, and anti-rotation tab 34 separates adjacent surface features. Each anti-rotation tab 34 may consequently be spaced apart by about 60 degrees. The surface feature 56 has a height in the range of about 1 to 4 mm and a length in the range of about 3 to 9.5 mm.

The superior wall 68 of positive surface feature 56 may extend over a distance of about 0.5 to 0.8 mm from outer surface 52 of lines 14. The canted intermediate wall 70 and the vertical intermediate wall 72 each may extend over a vertical distance 76 of about 1 to 3 mm. The length of the inferior wall 74 generally is in the range of about 1 to 1.5 mm. The height of the positive surface feature 56, measured from superior wall 68 to inferior wall 74, is about 1 to 4 mm.

As noted above, a deformable portion 64 of the surface feature 56 is separated from the outer surface 52 by a gap 66. The gap may span a distance 80 of about 0.5 to 2.0 mm.

As further illustrated in FIG. 11A, the positive surface feature 56 may be integrally formed with the outer surface 52 of liner 14. In one embodiment, the surface feature is integral with a superior portion 82 of outer surface 52. As such, the superior wall 68 and canted intermediate wall 70 extend from superior portion 82. The vertical intermediate wall 72, which has inner 72a and outer 72b portions, forms the deformable portion 64 of positive surface feature and is cantilevered such that it is separated from an inferior portion 84 of outer surface 52. In one embodiment, shown in FIG. 11A, the inferior portion 84 is recessed with respect to the superior portion 82. The inferior portion may be recessed by about 0.5 to 1.0 mm.

As noted above, the invention provides a reliable and convenient attachment mechanism for selectively joining an acetabular shell to a liner component. To attach these two components together, the anti-rotation tabs 34 of the liner 14 are aligned with the recesses 28 of the shell 12. This orientation allows the outer surface of the liner to be inserted through opening 62 into the inner surface of the shell 12. During the insertion process the canted intermediate wall 70 of the surface features 56 will encounter the inferior wall 86 of rim 26 of shell 12, resisting further insertion of the liner within the shell. This resistance to further insertion can be overcome by applying additional force to the liner, causing the deformable cantilevered portion 64 of the surface features 56 to deform. Such deformation allows the liner 14 and the surface features 56 to fit within the opening 62 of shell 12. Upon proper seating of the liner 12 within the shell, the deformable portion 64 returns to its original orientation and becomes seated within groove 24. This enables the liner to be mechanically engaged within the shell.

One of ordinary skill in the art will appreciate that the positive surface features 56 need not be overly pliable to effect insertion of the liner within the shell. The plurality of surface features 56 will depend on a number of variables including the size and shape of the surface features. Further, the geometry of the surface features 56 may be modified if necessary to accommodate ease of insertion.

It is understood that various modifications may be made to the invention described herein without departing from the intended scope thereof. Further, all dimensions are intended to serve only as examples; one of ordinary skill in the art may easily determine additional or alternative dimensions. All references cited herein are expressly incorporated by reference in their entirety.

What is claimed:

1. An acetabular cup assembly, comprising:
   a shell component having a generally convex bone-engaging outer surface and a generally concave inner surface with at least one groove formed in the inner surface thereof and extending about at least a portion of the circumference of the inner surface of the shell component;
   a liner component having an inner concave surface and an outer convex surface with a shape complementary to and matable within the inner surface of the shell component, the liner component having a polar region and an equator region; and
   at least one deformable positive surface feature unitary with the outer surface of the liner component, the at least one deformable positive surface feature having a superior wall, an inferior wall, a canted intermediate wall adjacent and inferior to said superior wall, and a vertical intermediate wall adjacent and inferior said canted intermediate wall, each of which protrudes from the outer surface of the liner component and wherein the inferior end is cantilevered such that an inner surface of the inferior wall is separated from the outer surface of the liner component by a gap,
   the liner component and the shell component being selectively, directly matable to each other by the engagement of the at least one deformable positive surface feature within the at least one groove.

2. The assembly of claim 1 wherein the at least one deformable positive surface feature comprises a plurality of positive surface features spaced at substantially equal intervals about a circumference of the liner component, in proximity to the equator region of the liner.

3. The assembly of claim 2 wherein the at least one groove comprises a plurality of grooves spaced at substantially equal intervals about a circumference of the shell component.

4. The assembly of claim 3 wherein each of the at least one grooves has a depth in the range of about 4 to 8 mm.

5. The assembly of claim 4 wherein each of the at least one grooves has a height in the range of about 2 to 4.5 mm.

6. The assembly of claim 5 wherein each of the at least one grooves is spaced apart from one another by about 0° to 180°.

7. The assembly of claim 3 wherein the at least one deformable positive surface feature protrudes from the outer surface of the liner component by a distance of about 1 to 3 mm.

8. The assembly of claim 7 wherein each of the at least one deformable positive surface features has a height in the range of about 1 to 4 mm.

9. The assembly of claim 8 wherein each of the at least one deformable positive surface features has a length in the range of about 3 to 9.5 mm.

10. The assembly of claim 3 wherein the gap has a width in the range of about 0.5 to 2 mm.

11. The assembly of claim 1, further comprising:
at least one anti-rotation tab member formed on the outer surface of the liner component, adjacent to the at least one deformable positive surface feature; and
at least one recess formed in the inner surface of the shell component, the at least one recess having a size and shape complementary to the at least one anti-rotation tab member such that each of the at least one recesses is effective to matingly engage one of the at least one anti-rotation tab members.

12. The assembly of claim 11 wherein each of the at least one anti-rotation tab members and the at least one recess is substantially hemispherically shaped.

13. The assembly of claim 1, wherein a diameter of the liner component measured from an outer surface of the at least one deformable positive surface feature is greater than an inner diameter of the shell component measured at an entrance to the inner surface of the shell component.

* * * * *